United States Patent [19]

Larsen et al.

[11] 4,154,971

[45] May 15, 1979

[54] DEUTERATED 1,1-DIFLUORO-2,2-DIHALOETHYL DIFLUOROMETHYL ETHERS

[75] Inventors: Eric R. Larsen; Leslie P. McCarty, both of Midland, Mich.

[73] Assignee: The Dow Chemical Company, Midland, Mich.

[21] Appl. No.: 882,498

[22] Filed: Mar. 1, 1978

Related U.S. Application Data

[63] Continuation-in-part of Ser. No. 803,926, Jun. 6, 1977, abandoned.

[51] Int. Cl.$^2$ .............................................. C07C 43/12
[52] U.S. Cl. .................................... 568/684; 424/342
[58] Field of Search ..................................... 260/614 F

[56] References Cited

U.S. PATENT DOCUMENTS

| | | | |
|---|---|---|---|
| 3,469,011 | 9/1969 | Terrell | 260/614 F X |
| 3,527,811 | 9/1970 | Terrell | 260/614 F |
| 3,527,812 | 9/1970 | Terrell | 260/614 F |
| 3,527,813 | 9/1970 | Terrell | 260/614 F |

Primary Examiner—Howard T. Mars
Attorney, Agent, or Firm—James W. Ambrosius

[57] ABSTRACT

Deuterated halo ethers useful as anesthetics and having lower toxicity than undeuterated analogues further including compositions, and methods of use.

4 Claims, No Drawings

DEUTERATED 1,1-DIFLUORO-2,2-DIHALOETHYL DIFLUOROMETHYL ETHERS

CROSS-REFERENCE TO RELATED APPLICATIONS

This application is a continuation-in-part of copending application Ser. No. 803,926 filed June 6, 1977, now abandoned.

BACKGROUND OF THE INVENTION

Various 1,1-difluoro-2,2-dihaloethyl difluoromethyl ethers have been described in the prior art and are known for use as inhalation anesthetics. See U.S. Pat. Nos. 3,469,011; 3,527,811; 3,527,812; and 3,527,813. The most commonly used is the compound 1,1,2-trifluoro-2-chloroethyl difluoromethyl ether also known as enflorane. Although the metabolic pathways of enflurane have not been defined, it is known the compound is metabolized in the body to produce inorganic fluorides in the blood which can cause renal dysfunction. See Barr et al., J. Pharmacol. Exp. Therap. 188, 257 (1974); Mazze et al., Anesthesiology 46, 265 (1977); and Eichhorn et al., Anesthesiology 45, 557 (1976). In addition, elevated levels of serum bromides released from metabolized material containing bromine is responsible for post-anesthetic depression.

SUMMARY OF THE INVENTION

The present invention is directed to novel deuterated analogues of the known 1,1-difluoro-2,2-dihaloethyl difluoromethyl ethers; the deuterated analogues have the general formula:

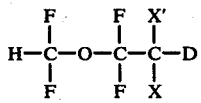

wherein X and X' represent a halogen selected from the group consisting of chloro, fluoro, and bromo with the proviso that when X is chloro X' is chloro or fluoro, and further when X is fluoro X' is bromo or chloro.

The present invention is also directed to a method of anesthetizing an animal, preferably a mammal, which comprises administering by inhalation an effective anesthetizing amount of a compound falling within the above general formula as a general inhalation anesthetic. As used herein, the term "animal" refers to an inhalation anesthetic susceptible animal.

The present invention is also directed to an anesthetic composition which comprises the minimum alveolar concentration of a compound falling within the scope of the present invention in combination with an innocuous gas vaporization medium and/or in combination with other anesthetics such as, for example, nitrous oxide. In anesthetizing an animal using the compounds, methods, and compositions described herein, the compound is usually administered by vaporizing the compound in the presence of an innocuous gas vaporization medium such as, for example, helium, nitrogen, oxygen, or various mixtures thereof. As used herein, the term "minimum alveolar concentration" refers to the effective concentration of the anesthetic or anesthetic combination required to produce the desired degree of anesthesia in the animal. The particular minimum alveolar concentration depends on factors well known in the art such as the animal to be anesthetized, the particular compound employed, etc.

Thus, it is seen three compounds fall within the scope of the present invention. They are as follows:

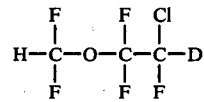

hereafter referred to as monodeuterated enflurane or 1,1,2-trifluoro-2-chloro-2-deuteroethyl difluoromethyl either;

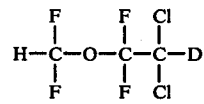

hereafter referred to as 1,1-difluoro-2-deutero-2,2-dichloroethyl difluoromethyl ether; and

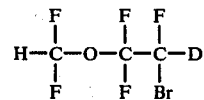

hereafter referred to as 1,1,2-1-trifluoro-2-bromo-2-deuteroethyl difluoromethyl ether.

The present invention is especially surprising in light of the fact that the monodeuterated analogue of methoxyflurane, i.e., the compound 1,1-difluoro-2,2-dichloro-2-deuteroethyl methyl ether, is more readily metabolized in the body to inorganic fluoride than the undeuterated compound. Thus, monodeuteration of methoxyflurane on the 2-carbon of the ethyl chain actually increases the toxicity of the compound.

DETAILED DESCRIPTION OF THE INVENTION

One method for preparing the 1,1-difluoro-2-deutero-2,2-dihaloethyl difluoromethyl ethers that are the subject of the present invention is by a base catalyzed deuterium exchange involving the hydrogen atom in the 2-ethyl position of the undeuterated anesthetic molecule. In this method the 1,1-difluoro-2,2-dihaloethyl difluoromethyl ether is mixed with heavy water ($D_2O$) in the presence of a strong base catalyst at a temperature and for a time sufficient to replace substantially all of the hydrogen in the 2-ethyl position of the anesthetic molecule with deuterium. Similar procedures are described in JACS 83, 1219 (1961) for the preparation of deuterated halothane. The hydrogen-deuterium exchange is an equillibrium reaction, therefore excess heavy water should be present to force the reaction in the direction of the deuterated anesthetic. In general, a ratio of about 10 parts heavy water to about 1 part anesthetic on a weight/weight basis will lead to substantially complete deuteration of the 2-ethyl position of the molecule.

The strong base catalyst is generally a soluble hydroxide or alkoxide of an alkali metal such as sodium or potassium. Alternately, a strong base ion exchange resin, such as for example Dowex[R] 21K (The Dow Chemical Co.), may be used to catalyze the reaction. The reaction mixture is allowed to react at a temperature of from about 25° to 150° C., with from about 50° to 100° C. being preferred, for a time sufficient to allow substantially all of the hydrogen to be replaced by deuterium on the anesthetic molecule. In general, the higher the reaction temperature the more quickly the exchange is completed. For relatively low boiling anesthetics such as enflurance (about 55° C.) correspondingly longer reaction times are required. To shorten the reaction time a pressurized reaction vessel may be employed to allow higher reaction temperatures. Phase transfer catalysis may also be used to increase the speed at which the reaction occurs.

The following examples will serve to further clarify the present invention but are not to be construed as a limitation thereon.

EXAMPLE 1

Preparation of Monodeuterated Enflurane

A 500 ml three-necked flask fitted with a reflux condenser and magnetic stirrer was charged with 100 ml of heavy water ($D_2O$) having 99.7% deuterium replacing the hydrogen, 5 grams of anhydrous sodium hydroxide, and 145 grams of enflurane. The mixture was heated at reflux (about 55° C.) for about 3 days. The reaction mixture was allowed to cool to room temperature. The ether was separated and dried over calcium chloride. The dry ether was distilled through a four inch vigreux column, and the fraction boiling at 56–57° C. was collected. NMR analysis confirmed this fraction as 90% deuterated enflurane.

EXAMPLE 2

Preparation of 1,1-Difluoro-2-Deutero-2,2-Dichloroethyl Difluoromethyl Ether

A reaction vessel similar to that used in Example 1 above was charged with 200ml of heavy water, 10 grams of anhydrous sodium hydroxide, and 200 grams of 1,1-difluoro-2,2-dichloroethyl difluoromethyl ether. The reaction mixture was refluxed at about 76° C. for about 1.5 hours. Bromine was added dropwise to the crude 1,1-difluoro-2-deutero-2,2-dichloroethyl difluoromethyl ether until the red bromine color persisted for several minutes. The resulting mixture was irradiated with a 275 watt sunlamp during bromine addition. The mixture was washed with dilute sodium hydroxide to remove the residual bromine, dried and distilled. The fraction boiling at 87° C. was collected. NMR analysis showed this fraction to be 93% $CF_2HOF_2CCl_2D$.

EXAMPLE 3

Preparation of 1,1,2-Trifluoro-2-Bromo-2-Deuteroethyl Difluoromethyl Ether

In the same manner as described in Examples 1 and 2 above, the reaction vessel was charged with 200 ml of heavy water, 10 grams of anhydrous sodium hydroxide and 200 grams of 2-bromo-1,1,2-trifluoroethyl difluoromethyl either. The reaction mixture was heated to reflux (about 67° C.) and held at that temperature for about 1.5 hours. The reaction mass was cooled after which the crude ether was separated and dried over calcium chloride. The dry ether was distilled, and the fraction boiling at about 72–73° C. was collected. NMR analysis showed this fraction to be greater than 96 percent 1,1,2-trifluoro-2-bromo-2-deuteroethyl difluoromethyl ether.

EXAMPLE 4

Metabolism studies for the presence of inorganic fluorides following the use of monodeuterated enflurane and enflurane were carried out as follows. Enflurane and monodeuterated enflurane were vaporized by metering the liquid compound at a controlled rate into a temperature regulated vaporization flask held at 150° C. The vapor was swept into the air inlet of a 30 liter glass exposure chamber at a rate of 6 liters/minute. The concentration of the anesthetic in the exposure chamber was monitored by gas-liquid chromatography using direct gas sampling loops.

Groups of 8 male Fisher rats (6 months of age, 250–300 grams) were exposed to room air (controls) and 2.5% volume/volume of enflurane and monodeuterated enflurane for a period of 3 hours. After exposure, the animals were removed immediately. All animals were maintained in individual metabolism cages for 48 hours after exposure. Urine was collected during each of two 24 hour intervals after exposure. No differences were noted between the anesthetic properties of enflurane and monodeuterated enflurane.

Urinary volume for each animal was recorded and the urine samples were assayed for inorganic fluoride using an Orion fluoride electrode.

A comparison of the amount of total inorganic fluoride in the urine of the control and test animals is shown in Table 1 below.

EXAMPLE 5

Using essentially the same technique as described in Example 4 above the compound 1,1,2-trifluoro-2-bromo-ethyl difluoromethyl ether was compared to its monodeuterated analogue prepared according to the method of Example 3. The rats were exposed to 1.5 percent volume/volume concentration of the control anesthetic and its deuterated analogue for a period of 3 hours. No differences were noted between the anesthetic properties of 1,1,2-trifluoro-2-bromoethyl difluoromethyl ether and the monodeuterated analogue.

Urine volume was recorded, and the urine was assayed for inorganic fluoride. The results are shown in Table I. In addition, after 48 hours the animals were sacrificed, and the blood was collected. Serum bromide ion concentrations were determined using an Orion bromide electrode. The results of the bromine determinations are shown in Table II.

EXAMPLE 6

Using essentially the same methods as described in Example 4 the compound 1,1-difluoro-2,2-dichloroethyl difluoromethyl ether and its mono-deuterated analogue were compared. Because of the potency of these anesthetics the rats were exposed to a concentration of only 0.5 percent volume/volume of the anesthetic and its mono-deuterated analogue. Again no differences in anesthetic properties were noted between 1,1-difluoro-2,2-dichloroethyl difluoromethyl ether and its mono-deuterated analogue.

The urine was collected and analyzed for inorganic fluoride concentration. The results are recorded in Table I.

TABLE I

| Example | Treatment | Urine Volume ml. 24 hrs. | Urine Volume ml. 48 hrs | Urinary Fluoride μM** 24 hrs | Urinary Fluoride μM** 48 hrs | Total Urinary Fluoride nM* |
|---|---|---|---|---|---|---|
|   | Room Air (Controls) | 9.2 ± 0.8 | 10.9 ± 2.6 | 0.9 ± 0.4 | 1.1 ± 0.2 | 20.6 ± 2.7 |
| 4 | CF$_2$HOCF$_2$CClFH | 14.8 ± 2.2 | 11.0 ± 1.9 | 4.3 + 0.7 | 1.6 + 0.2 | 80.7 ± 10.1 |
|   | CH$_2$HOCF$_2$CClFD | 10.9 ± 1.5 | 8.9 ± 1.5 | 1.7 ± 0.2 | 1.1 ± 0.1 | 28.6 ± 4.7 |
|   | Room Air (Controls) | 9.1 ± 1.0 | 8.5 ± 1.5 | 0.7 ± 0.1 | 0.8 ± 0.1 | 12.7 ± 0.7 |
| 5 | CF$_2$HOCF$_2$CFBrH | 12.8 ± 1.4 | 8.0 ± 1.5 | 10.4 ± 1.9 | 3.3 ± 0.7 | 156.8 ± 20.9 |
|   | CF$_2$HOCF$_2$CFBrD | 11.3 ± 1.9 | 7.4 ± 1.0 | 2.6 ± 0.9 | 1.3 ± 0.1 | 37.8 ± 5.8 |
|   | Room Air (Controls) | 10.3 ± 2.5 | 8.3 ± 2.8 | 0.7 ± 0.0 | 0.8 ± 0.1 | 14.2 ± 3.4 |
| 6 | CF$_2$HOCF$_2$CCl$_2$H | 14.6 ± 2.3 | 10.0 ± 2.1 | 1.4 ± 0.2 | 1.0 ± 0.1 | 30.2 ± 3.6 |
|   | CF$_2$HOCF$_2$CCl$_2$D | 12.2 ± 1.3 | 9.6 ± 1.6 | 1.1 ± 0.01 | 0.8 ± 0.1 | 21.5 ± 2.9 |

*Inorganic fluoride expressed in nanomoles (nM)
**Inorganic fluoride expressed as micromolar (μM)

TABLE II

| Treatment | Serum Bromine (millimolar) |
|---|---|
| Room Air (Controls) | 0.53 ± 0.02 |
| CF$_2$HOCF$_2$CFBrH | 1.59 ± 0.70 |
| CF$_2$HOCF$_2$CFBrD | 0.82 ± 0.09 |

The data indicate that animals treated with the monodeuterated 1,1-difluoro-2,2-dihaloethyl difluoromethyl ethers, that are the subjects of the present invention, show significantly lower concentrations of inorganic fluoride in the urine of the treated animals than in the urine of similar animals anesthetized using the undeuterated analogues. Likewise animals treated with 1,1,2-trifluoro-2-bromo-2-deuteroethyl difluoromethyl ether showed lower concentrations of inorganic bromide in the serum than the serum of animals treated with undeuterated anesthetic. The most dramatic differences were seen in the mono-deuterated enflurane and 1,1,2-trifluoro-2-bromo-2-deuteroethyl difluoromethyl ether where a decrease in organic fluoride of 65 percent and 76 percent, respectively, as compared to the undeuterated anesthetics was observed. Although less dramatic, a significant decrease (29 percent) was also observed for 1,1-difluoro-2-deutero-2,2-dichloroethyl difluoromethyl ether. Anesthetic potency coupled with a low release of inorganic fluoride into the blood make this latter compound the preferred embodiment of the invention.

We claim:

1. A compound of the formula

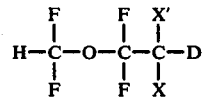

wherein X and X' represent a halogen selected from the group consisting of chloro, fluoro, and bromo with the proviso that when X is chloro X' is chloro or fluoro, and further when X is fluoro X' is bromo or chloro.

2. The compound of claim 1 which is 1,1,2-trifluoro-2-chloro-2-deuteroethyl difluoromethyl ether.

3. The compound of claim 1 which is 1,1-difluoro-2-deutero-2,2-dichloroethyl difluoromethyl ether.

4. The compound of claim 1 which is 1,1,2-trifluoro-2-bromo-2-deuteroethyl difluoromethyl ether.

* * * * *